United States Patent [19]

Partenheimer

[11] 4,020,174
[45] Apr. 26, 1977

[54] REACTIVATION OF MALEIC ANHYDRIDE PRODUCING PHOSPHORUS-VANADIUM-OXYGEN COMPLEX OXIDATION CATALYSTS BY TREATMENT WITH HALIDE CONTAINING MATERIALS

[75] Inventor: Walter Partenheimer, Naperville, Ill.
[73] Assignee: Standard Oil Company (Indiana), Chicago, Ill.
[22] Filed: Sept. 24, 1975
[21] Appl. No.: 616,370
[52] U.S. Cl. .......................... 260/346.8 A; 252/415
[51] Int. Cl.$^2$ ...................................... C07D 307/60
[58] Field of Search ................ 260/346.8; 252/413, 252/414, 415

[56] References Cited
UNITED STATES PATENTS
3,862,146  1/1975  Boghosian ...................... 260/346.8
FOREIGN PATENTS OR APPLICATIONS
1,291,354  10/1972  United Kingdom ............ 260/346.8

Primary Examiner—Henry R. Jiles
Assistant Examiner—Bernard Dentz
Attorney, Agent, or Firm—Robert E. Sloat; Arthur G. Gilkes; William T. McClain

[57] ABSTRACT

The present disclosure relates to a method of reactivation of certain catalytic properties of a phosphorous-vanadium-oxygen complex catalyst which is used for the oxidation of hydrocarbons in particular acyclic aliphatics such as alkanes or alkenes to oxidation products including aldehydes, ketones, acids and anhydrides. The present method of reactivation is implemented by passing a material containing a halide over the catalyst during noqmal oxidation operations or in a separate procedure for process improvements. A process using a phosphorous-vanadium-oxygen complex zinc promoted catalyst wherein butane is passed along with air or oxygen over said catalyst to effect the production of maleic anhydride is suitable for the claimed reactivating procedure.

48 Claims, No Drawings

REACTIVATION OF MALEIC ANHYDRIDE PRODUCING PHOSPHORUS-VANADIUM-OXYGEN COMPLEX OXIDATION CATALYSTS BY TREATMENT WITH HALIDE CONTAINING MATERIALS

BACKGROUND OF THE INVENTION

1. Field of the Invention

The field of art to which this invention pertains is reactivation of oxidation catalysts and in particular, the reactivation of phosphorous-vanadium-oxygen complex catalysts which are used for the production of oxygenated products including aldehydes, ketones, acids and anhydrides. In a specified instance the aforestated catalysts can be used for the production of maleic anhydride from butane.

2. Description of the Prior Art

Relevant prior art includes U.S. Pat. No. 2,773,921 issued Dec. 11, 1956, having inventors Paul N. Rylander, Jr. and Wilford J. Zimmerschied. This patent was officially classified in Class 260-683.15 and generally relates to a phosphoric acid-vanadium pentoxide catalyst and a hydrocarbon conversion process using such a catalyst. In general, the patent teaches and discloses the use of a catalyst produced from the reaction of vanadium pentoxide and certain anhydrous phosphoric acids. It is especially directed towards polymerization processing. More specifically, the catalyst described and claimed in this reference is a reaction product of vanadium pentoxide and an acid selected from the group consisting of anhydrous orthophosphoric, pyrophosphoric or triphosphoric acids.

Other art which may be pertinent includes the use of chlorides or chlorine in maintaining catalyst activity in reforming or other similar processing. In the case of reforming, chloride addition is utilizedd to maintain a certain chloride level on the catalyst thereby keeping its acidity high enough for sufficient hydrocracking of paraffins.

SUMMARY OF THE INVENTION

The present invention can be summarized as a process improvement in a process for the production of oxidation products from feed materials generally comprising alkanes or alkenes or in some instances aromatics which comprises contacting a hydrocarbon feed and an oxygen containing gaseous stream with a catalyst complex which comprises phosphorous-vanadium-oxygen and has from about 0.5 to about 5 atoms of phosphorous for each atom of vanadium and in a more limited instance from about 0.05 to about 0.5 atoms of metal promoter for each atom of vandium. In the processing, the selectivity of the catalyst for the production of desired oxidation products becomes decreased through mechanisms not necessarily thoroughly understood. The improvement in the above stated general process includes contacting the catalyst complex with an effective amount of a reactivating agent which is selected from the group consisting of molecular halogens, and certain compounds containing at least one halide radical or mixtures thereof to thereby increase the selectivity of the catalyst for subsequent processing.

A broad embodiment of this invention resides in a process for the preparation of selected oxygenated product selected from the group consisting of alkanes, alkenes, or mixtures thereof or aromatics which comprises contacting said feed material and a gas containing molecular oxygen in the vapor phase with a catalyst comprising a phosphorous-vanadium-oxygen complex having from about 0.5 to about 5 atoms of phosphorous for each atom of vanadium, wherein the improvement which comprises contacting said catalyst complex at reactivating conditions with an effective amount of a reactivating agent selected from the group consisting of:

A. Molecular halogens;

B. Organic halides being in the vapor state above about 250° C. at atmospheric pressure represented by the formula:

where each X is selected halie and $n$ is an integer from 1 to 4, any remaining radicals being hydrogen;

C. Organic halides being in the vapor state above about 250° C. at atmospheric pressure represented by the formula:

where R is alkane, alkene or alkyne of straight or branched structure having at least two carbon atoms and $X_1$, is independently a primary, secondary or tertiary halide and $m$ is an integer of from 1 to about 20 consistent with the number of carbon atoms of said structure;

D. Hydrogen halides;

E. Main group metal halides selected from the group consisting of $PCl_3$, $PCl_5$, $VF_4$, $VF_5$ or mixtures thereof; or mixtures thereof to thereby enhance the selectivity of the catalyst for the production of selected oxygenated products.

Another embodiment of the invention resides in a process for the production of oxidation products by the oxidation of feed hydrocarbons selected from the group consisting of alkanes or alkenes or aromatics or mixtures thereof which comprises contacting said feed hydrocarbons and a gas containing molecular oxygen in the vapor phase with a phosphorous-vanadium-oxygen complex metal promoted catalyst, said catalyst complex having from about 0.5 to about 5 atoms of phosphorous for each atom of vanadium and from about 0.05 to about 0.5 atoms of metal promoter for each atom of vanadium, wherein the selectivity of the catalyst for production of oxidation products from said hydrocarbons has decreased from a level achieved during earlier catalyst life of said catalyst complex, wherein the improvement which comprises contacting said catalyst complex with an effective amount of a reactivating agent selected from the group consisting of molecular halogens, certain compounds containing at least one halide radical or mixtures thereof to thereby increase said selectivity of the catalyst for production of oxidation products.

In another embodiment the present invention relates to an improvement in a process for the preparation of maleic anhydride which comprises contacting a hydrocarbon containing at least about 50 percent by weight n-butane and a gas containing molecular oxygen in the vapor phase with catalyst comprising a phosphorous-vanadium-oxygen complex and a zinc metal promoter, said catalyst complex having from about 0.5 to about 5 atoms of phosphorous for each atom of vanadium and from about 0.05 to about 0.5 atoms of zinc promoter for each atom of vanadium, wherein the selectivity of the catalyst for production of maleic anhydride from butane has decreased from a selectivity level achieved during earlier catalyst life of said catalyst complex, wherein the improvement which comprises contacting said catalyst complex at reactivating conditions with an effective amount of a reactivating agent selected from the group consisting of chlorine, hydrogen chloride, lower alkyl halides including carbon tetrachloride, phosphorous trichloride or mixtures thereof to thereby subsequently increase said selectivity of the catalyst for maleic anhydride production.

DETAILED DESCRIPTION OF THE INVENTION

The present invention generally relates to an improved process wherein the selectivity of a specified oxidation catalyst can be improved or maintained at initial selectivity levels by the addition of certain reactivating agents to the catalyst during processing or in a separate reactivating procedure. In particular, the invention can be employed in most oxidation processes and specifically in oxidation processing wherein maleic anhydride is produced from butanes and/or butenes. The catalyst utilized in the improved process includes a phosphorous-vanadium-oxygen complex catalyst which in some instances contains a metal promoter. In a specific instance, the metal promoter is selected from the group consisting of zinc, bismuth, copper, lithium, or mixtures thereof.

The specified catalyst for use in oxidation processing, and in particular the production of maleic anhydride or other similar oxygenation products, is described in detail along with methods of production and its process use in U.S. Pat. No. 3,862,147 issued Jan. 21, 1975, having Edward M. Boghosian as its inventor and assigned to Standard Oil Company (Indiana). The above cited patent is hereby incorporated into this specification by specific reference thereto.

The invention of U.S. Pat. No. 3,862,146 described above can be summarized as an oxidation process using a phosphorous-vanadium-oxygen complex metal promoted catalyst for the production of oxygenated products and in particular maleic anhydride.

The above cited patent can be abstracted as follows:
The oxidation of butane to maleic anhydride in the presence of a phosphorous-vanadium-oxygen complex catalyst is enhanced by the addition to the catalyst of a zinc, bismuth, copper or lithium metal activator. The yield of the oxidation may be increased by as much as 50% without any loss in selctivity to the production of maleic anhydride.

There are no drawings in the reference patent and accordingly none are submitted herewith.

The broadest claim of said referenced U.S. Patent is included below:

A process for the preparation of maleic anhydride which comprises: contacting a feedstock consisting essentially of 50% at least N-butane and a gas-containing molecular oxygen in the vapor phase with a catalyst complex cosisting essentially of phosphorous-vanadium-oxygen and a metal activator selected from zinc, copper, bismuth, lithium or mixtures of these, said catalyst complex comprising from about 0.5 to 5 atoms of phosphorous for each atom of vanadium and from 0.05 to 0.5 atoms of said metal activator for each atom of vanadium.

While the above reference patent does specifically describe a certain process and catalyst using such process, the present disclosure is not necessarily limited to all stated limitations of such patent.

Basically the present invention can incorporate catalysts generally as described in the referenced patent along with other phosphorous-vanadium-oxygen complex catalysts which may contain additional and different metal promoters (activators) and/or other components.

In order to more adequately understand and describe the various catalytic properties which are effected through the use of the catalyst described and used in this invention, the following definition of terms is presented.

$$\text{Conversion} = \frac{\text{moles hydrocarbon feed consumed}}{\text{moles hydrocarbon charged}} \quad (1)$$

$$\text{Selectivity} = \frac{\text{moles desired oxidation product produced}}{\text{moles hydrocarbon feed consumed}} \quad (2)$$

$$\text{Mole Yield} = (\text{Conversion})(\text{Selectivity}) \quad (3)$$

In a specific instance wherein a feed stream containing essentially normal butane is charged to the reaction zone for the production of maleic anhydride the conversion, selectivity and mole yield are shown in the equations below.

$$\text{Conversion} = \frac{\text{moles n-C}_4 \text{ consumed}}{\text{moles n-C}_4 \text{ charged}} \quad (4)$$

$$\text{Selectivity} = \frac{\text{moles maleic anhydride produced}}{\text{moles n-C}_4 \text{ consumed}} \quad (5)$$

6. Mole yield = (Conversion) (Selectivity)

In instances in which a weight yield is desired for the production of maleic anhydride from normal butane the following calculation can be used.

7. Weight Yield = (Conversion) (Selectivity) (1.69)

The above conversion, selectivity and yields on the molar basis times 100 equal percentage conversion, selectivity and mole yields. When determining a weight yield it is necessary to know the ratio of the molecular weights of the feed hydrocarbon and the oxygenation product and accordingly the weight yield for the production of maleic anhydride from normal butane is defined as the product of the molar conversion times the molar selectivity (for normal butane to maleic anhydride) all times 1.69. The theoretical maximum production of maleic anhydride from normal butane would give a weight yield of 1.69 pounds of maleic anhydride for each pound of normal butane consumed assuming 100 percent selectivity and conversion. In stating the weight yield on a percentage basis, it merely reflects the quantity of theoretical weight yield of maleic anhydride times 100. Accordingly then, the theoretical weight percent yield would be 169 percent.

When using the above described catalyst in a specific process for the production of maleic anhydride from a hydrocarbon feed containing normal butane, there appears after a certain period of catalyst life a decrease in the selectivity of the catalyst from the production of maleic anhydride from normal butane. The selectivity decrease is accompanied by increased production of non-maleic anhydride oxygenated products, namely, carbon monoxide and carbon dioxide decreasing the yield of maleic anhydride. There may also be instances in which both selectivity and conversion decrease greatly reducing the actual yield of maleic anhydride product.

Accordingly then, the present invention is presented as a process improvement whereby a reactivating agent, as will be described in more detail below, is either added to the feed stream or is separately contacted with the catalyst to increase the selectivity of the catalyst to levels approaching or at least equal to those measured for fresh catalyst. Such selectivity improvement increases the yield of oxygenated product resulting in more efficient and profitable operations.

The reactivating conditions which are contemplated for use in the improved reactivating process of this invention include the use of an effective amount of a reactivating agent to contact said catalyst and thereby cause at least its selectivity to be increased for the more efficient production of desired oxidation product or products. The reactivating agents which will be more completely described below may either be incorporated into the feed stream passing into the reaction zone or may contact the catalyst in a separate processing procedure. In some instance both operations may be used.

The concentration of the activating agent passing over the catalyst should be monitored so as to prevent damage to the catalyst from excess additions. Additional problems associated with activating agent additions include the production of corrosive end products which possibly could damage plant equipment.

It is also contemplated, whether the reactivating agent is added to the feed passing into the reaction zone or in a separate step, to employ associated processing equipment so as to eliminate passage of noxious products to the environment through the use of suitable scrubbing and/or vapor recovery means.

It has been found in determining what is an effective amount of reactivating agent that there is some minimum concentration of the reactivating agent which should be passed into the reaction zone to effect the increase in selectivity of the catalyst. However, it is difficult to ascertain the concentration as an absolute quantity since reactor designs would have a substantial influence on the actual concentration to which the catalyst within the reaction zone would be exposed. Accordingly then, the better approach would be to state that a minimum total quantity based generally on the phosphorous and/or vanadium content in the reaction zone be passed into the reaction zone for reactivating conditions to give the necessary selectivity increase.

Carrier gases are contemplated when the reactivating procedure occurs as a separate step to move the reactivating agent through the catalyst bed. Such carrier gases can be used as a substitute for the normal feedstock passing into the reaction zone. The carrier gases are not necessarily critical in their choice and can include materials such as nitrogen, butane, oxygen, or any other available gaseous stream which would be compatible with the reactivating agent and would not degrade the catalyst performance.

If a separate reactivating step is used it is contemplated that before or after passage of reactivating agent through the catalyst bed that a gas purge be used to remove entrained reactivating agent and other materials from the catalyst. Such purge materials can include nitrogen or other inert gases or light hydrocarbons such as butane.

When utilizing certain catalysts for the production of maleic anhydride from rich normal butane streams, it has been found after the reactivation of the catalyst in a separate processing sequence (using a carbon tetrachloride reactivating agent) that a steam treatment improves the conversion level of the catalyst. The exact mechanism taking place which allows the steam purge after reactivating procedures to additionally enhance catalyst performance are not specifically known. Evidence indicates that when using alkyl halides as reactivating agents that at certain temperatures a small amount of carbon residue is laid down on the catalyst adversely affecting its conversion. Accordingly then, it is theorized that the passage of steam over a catalyst in the absence of the reactivating agent will cause a water gas reaction to take place effectively removing the deposited carbon from the catalyst and allowing an enhanced weight yield to be obtained.

The reactivating temperatures will depend on many factors including whether the reactivating agent is added to the feed in an essentially on-stream operation or whether the reactivating agent is contacted with the catalyst reaction zone in a separate processing step. Of course, when the reactivating agent is present in the feedstock, the temperature of the reaction zone will generally be maintained as that necessary for reasonably efficient and economical production of oxygenation products. When however, the reactivating agent is passed througyh the catalyst reaction zone in a separate reactivating procedure, large temperature variations may take place.

Specifically the temperatures for reactivation should be in the range generally from about 300° to about 650° C. In a most preferred instance, the reactivating conditions should include a temperature within the range of from about 300° to about 550° and in some instances from about 300° to about 500° C. Of course, the temperatures of reactivation will vary depending on the specific catalyst and oxidation process utilized. In a specific instance in which a normal butane feed is passed into the reaction zone for the production of maleic anhydride, it has been found that a most preferred reactivating temperature will be somewhere above 300° C but below 500° C. when a carbon tetrachloride reactivating agent is used.

For the most successful reactivation of a butane oxidation catalyst for producing maleic anhydride when using a carbon tetrachloride reactivating agent it has been found that reactivation temperatures greater than about 300° C. are needed to cause increases in selectivity but less than about 400° C. are needed to prevent excessive losses in catalyst conversion unless a subsequent steam treatment takes place.

The reactivating agents which may be used in the reactivating procedure claimed herein generally include materials such as molecular halogens or mixtures thereof, or compounds containing one or more halide radicals or mixtures thereof. However, within the broad category of halides there obviously exists materials with hazardous properties such as self-detonation or extremely corrosive materials which while within the definition of halides for reactivating agents would not be effective since they destroy the catalyst and/or the processing equipment. Accordingly then in defining the halides as used herein, the inoperative species are to be precluded.

One of the basic requirements when utilizing the halide materials as reactivating agents is that they remain in a vapor phase when employed at reactivating conditions. Accordingly then, materials which have reasonably high boiling points are not suitable and would present processing difficulties. It is preferable that the halide materials be in a vapor phase at temperatures above a minimum of about 250° C. at atmospheric pressure. The specific reactivating agents can include pure components or mixtures of components. Specifically utilizable in the reactivating process herein are halides including the gaseous forms of fluorine, chlorine, and bromine. In some instances gaseous iodine may be used but its boiling point is sufficiently high so that it may not present a favorable reactivating agent when used at low temperatures. Specific reactivating agents can include but are not necessarily limited to the following: hydrogen chloride, trichloromethane, dichloromethane, monochloromethane, hexachloroethane, halide substituted ethanes, propanes, butanes (normal or iso), pentanes (normal or branched), hexanes (branched or straight), and other chloride or halide containing aliphatics. Other specific halides which can be utilized include materials such as 1,6-dichlorohexane, 1,2-dichlorohexane, 1,2-dibromohexane, 2,2-dichlorohexane, 2,3-dichlorohexane, 2,5-dichlorohexane, and 3,4-dichlorohexane, normal hexylbromide, sec-hexylbromide and 3-bromohexane.

Organic halides of fairly low carbon number (generally 4 or less) are preferred to reduce the possibility of coke formation during reactivation.

Inorganic materials include trifloroacetic acid, $POCl_3$, $Cl_2O_7$, $PCl_5$, $VF_5$, $VF_4$. In a preferred instance the reactivating agents should be non-metal halides.

Inter halogens which may be utilized include gases which have reasonably low boiling points such as ClF, $ClF_3$, BrF, BrCl, IBr, $BrF_5$, $F_2O$, $Cl_2O$, $ClO_2$ (potentially explosive), $Cl_2O_6$, $Cl_2O_7$, $Br_2O$, and oxy acids of chlorine, bromine, and iodine. Other materials which may be utilizable at high reactivation temperatures include products such as $CF_4$, $CHF_3$, Freon 12, Freon 13, Freon 22, Freon 21 and trichloro acetic acid.

These and other halogen or halide-containing materials may be utilized in addition to those described above.

The feed materials which can be used include alkanes, alkenes and aromatics which are generally converted to maleic anhydride as the selected oxygenated product. Of the aromatics benzene is generally preferred for maleic anhydride production. Normal butane is the preferred alkane especially in relatively high concentrations. In an especially preferred instance, the feed material should contain over 50 weight percent of its total hydrocarbon content as normal butane. Mixtures of butanes with butene or butadiene may be used.

In some cases ortho-xylene can be used as a feed in which instance the selected oxygenated product is phthalic anhydride.

It is possible to operate the oxidation process by maintaining the concentration of the feed material in oxygen either above or below the explosive limit concentrations for the given system.

The following examples are presented to specifically illustrate certain embodiments of the claimed invention and are not presented so as to unduly limit the scope of the claims.

EXAMPLE 1

In this example a catalyst which had been contacted with a butane and air mixture for a certain period of time was reactivated with a carbon tetrachloride treatment and thereafter put back on stream to show the effects of the halide treatment on the spent catalyst. There was an improvement in yield and selectivity as a result of such a treatment.

The carbon tetrachloride treatment was performed by adding the carbon tetrachloride to the normal butane and air feed mixture. The feed stream contained approximately 1.1 volume percent of normal butane feed in an artificially formulated air atmosphere. The feed stream was passed through a reactor which contained a catalyst as described in this specification and had a phosphorous to vanadium atomic ratio of about 1.2 and a zinc metal promoter present in an atomic ratio with respect to vanadium of about 0.2. During normal operations the weight hourly space velocity of the feed containing butane and air was regulated at about 1.4 at atmospheric pressure. The same space velocity and pressure was maintained when carbon tetrachloride additions were made to the feed stream.

During a thirty minute period for carbon tetrachloride treatment the 1.1 volume percent butane feed stream was passed through a scrubber which contained liquid carbon tetrachloride maintained at 0° C. and thereafter into the reaction zone which was maintained at 400° C. temperature. Vapor pressure calculations indicated that the feed passing into the reaction zone contained about 4.1 volume percent concentration of carbon tetrachloride. The carbon tetrachloride treatment as shown in the Table 1 below causes a substantial improvement in selectivity of the catalyst for the production of maleic anhydride after about 22 hours operation. Also included in the data shown in Table 1 is the performance of the original fresh catalyst at 420° C. reaction temperatures and the temperature of a spent catalyst showing the conversion selectivity and weight yields at 450° reactor temperatures prior to the reactivating procedure.

TABLE 1

| TIME ON STREAM, HRS | REACTOR TEMP., °C. | CONVERSION PERCENT | SELECTIVITY PERCENT | WEIGHT YIELD PERCENT |
|---|---|---|---|---|
| Original fresh catalyst | 450 | 83 | 62 | 87 |
| Spent catalyst | 450 | 94 | 27 | 43 |
| 18 | 400 | 82 | 50 | 69 |
| (Cl$_4$ Treament (30 mins.) | 450 | — | — | — |
| 40 | 400 | 22 | 76 | 29 |
| 66 | 450 | 79 | 60 | 80 |
| 90 | 450 | 86 | 59 | 86 |
| 186 | 450 | 94 | 52 | 83 |
| 216 | 420 | 97 | 60 | 89 |
| 379 | 420 | 88 | 60 | 89 |
| 499 | 410 | 88 | 59 | 88 |

TABLE 1-continued

| TIME ON STREAM, HRS | REACTOR TEMP., ° C. | CONVERSION PERCENT | SELECTIVITY PERCENT | WEIGHT YIELD PERCENT |
| --- | --- | --- | --- | --- |
| 1948 | 400 | 77 | 61 | 80 |

EXAMPLE 2

In this example approximately 10 grams of a spent maleic anhydride catalyst having the same essential composition as that described for the catalyst in Example 1 was placed in a glass-lined tubular oven, blanketed with a flow of nitrogen gas and heated to 400° C. The nitrogen stream was then passed through a solution of concentrated aqueous hydrochloric acid at room temperature. The acid saturated stream was then passed into the tubular oven. Four hours later at 400° C, the hydrogen chloride treatment was terminated and the catalyst was cooled down under a stream of pure nitrogen gas. The catalyst was loaded into a small reactor similar in operation to that described for Example 1 and fed a 1.1 percent normal butane in air feed stream at a weight hourly space velocity of 1.4 at a temperature of 400° C. and atmospheric pressure. Reported results for conversion, selectivity and yields are shown for both the spent catalyst prior to the hydrogen chloride treatment and for the treated catalyst at up to 230 hours of on stream operation.

TABLE 2

| TIME ON STREAM, HRS. | REACTOR TEMP., ° C. | CONVERSION PERCENT | SELECTIVITY PERCENT | WEIGHT YIELD PERCENT |
| --- | --- | --- | --- | --- |
| SPENT CATALYST | 400 | 77 | 56 | 73 |
| 18 | 400 | 73 | 66 | 82 |
| 41 | 400 | 74 | 69 | 86 |
| 185 | 400 | 76 | 69 | 88 |
| 233 | 400 | 76 | 67 | 86 |

EXAMPLE 3

In this example the in-situ addition of hydrogen chloride to an on-stream reaction zone was performed. A beneficial effect on the catalyst was observed. During the on-stream reaction a feed stream containing approximately 1.1 volume percent of normal butane in air was passed over a catalyst which was maintained at a temperature of about 400° C., a pressure at atmospheric and a weight hourly space velocity of about 1.4. At various intervals during the reaction of butane to maleic anhydride, hydrogen chloride was passed in admixture with the feed stream over the catalyst bed. The hydrogen chloride treatment took place by first passing the feed stream at essentially atmospheric pressure through a gas scrubber which contained concentrated aqueous hydrochloric acid at room temperature. The air and butane stream essentially saturated at room temperature with hydrogen chloride was then passed into the reaction zone for periods of time as indicated in Table 3 below. After four successive hydrogen chloride treatments the overall yield and selectivity of the catalyst had been substantially improved. The specific results of such on-stream chloride treatment are shown in Table 3 below.

TABLE 3

| TIME ON STREAM, HRS. | REACTOR TEMP., ° C. | CONVERSION PERCENT | SELECTIVITY PERCENT | WEIGHT YIELD PERCENT |
| --- | --- | --- | --- | --- |
| 257 | 400 | 77 | 51 | 67 |
| 263 | 400 | — | — | — |
| (30 min. HCl) | | | | |
| 281 | 400 | 76 | 54 | 70 |
| 286 | 400 | — | — | — |
| (20 min. HCl) | | | | |
| 288 | 400 | 75 | 53 | 66 |
| 305 | 400 | 75 | 56 | 71 |
| 310 | 400 | — | — | — |
| (20 min. HCl) | | | | |
| 312 | 400 | 75 | 53 | 67 |
| 329 | 400 | 75 | 58 | 73 |
| 333 | 400 | — | — | — |
| (35 min. HCl) | | | | |
| 425 | 400 | 74 | 59 | 74 |

EXAMPLE 4

In this example catalyst similar to that described in Example 1 was used to illustrate the effects of gaseous chloride treatments on catalytic performance.

During normal processing a 1.1 volume percent n-butane in synthetic air feed was passed through a reactor at atmospheric pressure and a regulated weight hourly space velocity of about 1.4. At certain intervals (17, 45, 179, 212 and 227 hours on stream) a gaseous stream of essentially pure chlorine was passed over the catalyst bed at a 1.4 weight hourly space velocity for periods of time ranging from 1 to 30 minutes. Then the feed was resumed and after a period of time ranging from 3 to 28 hours a gas chromatograph analysis was run on the effluent for purpose of determining the influence of chloride on the catalyst.

The results of this testing are reported in Table 4 below and indicate chlorine does improve the yield somewhat but the selectivity is not increased as much as would be expected from a carbon tetrachloride treatment at the same temperature.

riods. The air contacting was performed to accelerate the catalyst deactivation so that a more rapid evaula-

TABLE 4

| TIME ON STREAM HRS. | | REACTOR TEMP., ° C. | CONVERSION PERCENT | SELECTIVITY PERCENT | WEIGHT YIELD, PERCENT |
|---|---|---|---|---|---|
| INITIAL CATALYST | | 454 | 99 | 33 | 55 |
| 17 | ($Cl_2$ Treatment, 1 minute) | 450 | — | — | — |
| 28 | | 452 | 96 | 39 | 63 |
| 45 | ($Cl_2$ Treatment, 5.5 minutes) | 450 | — | — | — |
| 48 | | 454 | 93 | 47 | 74 |
| 179 | ($Cl_2$ Treatment, 18 minutes) | 450 | — | — | — |
| 185 | | 448 | 94 | 47 | 74 |
| 212 | ($Cl_2$ Treatment, 10 minutes) | 459 | — | — | — |
| 215 | | 448 | 89 | 48 | 73 |
| 227 | ($Cl_2$ Treatment, 30 minutes) | 450 | — | — | — |
| 233 | | 447 | 87 | 47 | 70 |
| 257 | | 416 | 75 | 61 | 78 |

EXAMPLE 5

In this example a catalyst identical to that described for Example 4 was contacted with essentially 100 percent chlorine gas for a three hour period at atmospheric pressure and a weight hourly space velocity of about 0.3.

At 65 hours on stream with feed at conditions identical to those described in Example 4, the catalyst was found to possess a conversion of 99 percent, a selectivity of 29 percent and a weight yield of 48 percent at 454° C. After the three hour chlorine treatment and after 46 more hours of feed processing, the catalyst gave a conversion of 100 percent, a selectivity of 16 percent and a weight yield of 27 percent, all measured at 450° C.

These data suggest that extensive chlorine treatments with high chlorine concentrations do not help catalyst performance and in fact actually harms its performance.

Lower concentrations of chlorine and/or reduced contact times can be beneficial as illustrated in Example 4 above.

EXAMPLE 6

In this example repetitive regenerations of a catalyst essentially identical to that used in Example 4 were performed to illustrate the effectiveness of repeated carbon tetrachloride treatments and the use of a steam purge to modify catalytic properties.

The normal on-stream n-butane oxidation operations were at conditions essentially the same as described in Example 4 above. The carbon tetrachloride treatment took place after the n-butane-air feed mixture was switched to a ½ hour nitrogen purge. After the carbon tetrachloride treatment had taken place, the ½ hour nitrogen purge took place again. The n-butane-air feed mixture was then restarted and conversion, selectivity and yield measurements were taken at the indicated temperatures and time periods.

The carbon tetrachloride reactivation took place at the indicated catalyst temperature by injecting into a nitrogen purge flowing at a weight hourly space velocity of 1.4, 0.07 ml of carbon tetrachloride in a 15 second time period.

During various segments of catalyst life the butane in the feed stream was stopped and essentially pure air was allowed to contact the catalyst for extended petion of the effectiveness of the halogen reactivation using carbon tetrachloride could be demonstrated. The air contacting has all the qualitative characteristics of a normally spent catalyst i.e., a decline in selectivity and $CO/CO_2$ molar ratio, and an increase in conversion.

After some of the carbon tetrachloride reactivation procedures were completed a steam treatment took place to illustrate its beneficial influence on catalyst performance. The steam treatment took place by passing over the catalyst at the indicated temperature a mixture of 85 volume percent water in nitrogen at a weight hourly space velocity of about 1.4 for the indicated time period. After the steam treatment, the normal feed of butane in air was passed over the catalyst and measurements were made of the conversion, selectivity and yield values.

The results of the above procedures are reported in Table 5 below and indicate that the catalyst appears to become more difficult to deactivate by the air treatment after each successive carbon tetrachloride reactivation.

In Table 5 below the stated treatment took place at the indicated period of catalyst life. All catalyst conversions, selectivities and yields are reported on the above described n-butane-air mixture. The temperatures for the various treatments were maintained as close to 460° C. as possible to allow a maximum number of process changes without the need to heat or cool the catalyst or feed.

The various sequences of reactivation shown in Table 5 illustrate the marked improvement in performance, especially selectivity of the catalyst, when the reactivation procedure is utilized. It is contemplated that by temperature manipulation that additional improvements in selectivity and yield would result.

The carbon tetrachloride treatment by itself at 67, 119, 240, 288, 454 and 617 hours catalyst life all resulted in substantial increases in selectivity of the catalyst. In the instances in which yields were reduced, additional time and/or subsequent steam treatment would increase conversion thereby increasing the ultimate yield of maleic anhydride.

The combination of carbon tetrachloride treatment at 617 hours and steam treatment at 644 resulted in a very substantial increase in yield (from 51 to 88 percent) with only a small decrease in selectivity.

The carbon tetrachloride and steam treatments at 751 and 753, and 777 and 844 hours respectively resulted in increases in overall yield with either stable or very slight losses in selectivity. The carbon tetrachloride and steam treatment performance at 940 hours increased both the conversion and the selectivity of the catalyst.

The final carbon tetrachloride treatment (991 hours) increased the selectivity while adversely affecting the conversion. The subsequent steam treatment at 1083 hours, however, more than doubled conversion resulting in an ultimate weight yield of 92 percent. This data illustrates the need in certain instances of a steam or functionally similar contacting of the catalyst after carbon tetrachloride treatment.

EXAMPLE 7

In this example carbon tetrachloride reactivations were performed under conditions essentially similar to those described in Example 6 on a catalyst described in Example 1. Within four hours of each carbon tetrachloride activation the conversion, selectivity and yields were determined. Some of the tests were repeated to illustrate the effects on catalyst performance of multiple carbon tetrachloride activation. In the 330° C. activation test the reaction zone temperature was reduced to 409° C. from 450° C. in one instance to illustrate the effects of temperature manipulation on catalyst performance.

TABLE 5

| OPERATION | TIME ON STREAM HRS. | REACTOR TEMP., °C. | CONVERSION PERCENT | SELECTIVITY PERCENT | WEIGHT PERCENT |
|---|---|---|---|---|---|
| Feed | 65 | 460 | 99 | 29 | 51 |
| CCl$_4$ Treatment | 67 | 460 | — | — | — |
| Feed | 72 | 459 | 63 | 60 | 64 |
| Feed | 89 | 460 | 83 | 58 | 81 |
| 3 hr. Air Treatment | 92 | 460 | — | — | — |
| Feed | 113 | 462 | 96 | 36 | 58 |
| CCl$_4$ Treatment | 119 | 460 | — | — | — |
| Feed | 137 | 461 | 85 | 56 | 80 |
| 3 hr. Air Treatment | 235 | 460 | — | — | — |
| Feed | 239 | 461 | 97 | 40 | 66 |
| CCl$_4$ Treatment | 240 | 460 | — | — | — |
| Feed | 257 | 460 | 66 | 60 | 67 |
| 5 hr. Air Treatment | 258 | 460 | — | — | — |
| Feed | 282 | 462 | 96 | 48 | 78 |
| CCl$_4$ Treatment | 288 | 460 | — | — | — |
| Feed | 289 | 461 | 54 | 61 | 56 |
| Feed | 425 | 462 | 83 | 56 | 78 |
| 4 hr. Air Treatment | 449 | 460 | | | |
| Feed | 453 | 460 | 93 | 53 | 83 |
| CCl$_4$ Treatment | 454 | 460 | — | — | — |
| Feed | 455 | 458 | 50 | 63 | 54 |
| Feed | 569 | 461 | 69 | 58 | 67 |
| 6.5 hr. Air Treatment | 570 | 460 | — | — | — |
| Feed | 597 | 460 | 81 | 54 | 74 |
| CCl$_4$ Treatment | 617 | 460 | — | — | — |
| Feed | 619 | 461 | 47 | 63 | 51 |
| 2.8 Hr. Steam Treatment | 645 | 460 | — | — | — |
| Feed | 665 | 462 | 91 | 57 | 88 |
| 8. Hr. Air Treatment | 668 | 460 | — | — | — |
| Feed | 750 | 461 | 96 | 49 | 79 |
| CCl$_4$ Treatment | 751 | 461 | — | — | — |
| Feed | 753 | 460 | 45 | 66 | 50 |
| 1.3 hr. Steam Treatment | 753 | 460 | — | — | — |
| Feed | 771 | 462 | 86 | 58 | 85 |
| 5 hr. Air Treatment | 771 | 460 | — | — | — |
| CCl$_4$ Treatment | 777 | 460 | — | — | — |
| Feed | 801 | 460 | 48 | 67 | 54 |
| Feed | 843 | 459 | 51 | 67 | 57 |
| 3 hr. Steam Treatment | 844 | 460 | — | — | — |
| Feed | 847 | 463 | 80 | 67 | 91 |
| 17 hr. Air Treatment | 909 | 460 | — | — | — |
| Feed | 916 | 462 | 91 | 54 | 82 |
| CCl$_4$ followed by 2.5 hr. steam treatment | 940 | 460 | — | — | — |
| Feed | 964 | 462 | 89 | 57 | 86 |
| 16 hr. Air Treatment | 970 | 460 | — | — | — |
| Feed | 990 | 462 | 92 | 54 | 84 |
| CCl$_4$ Treatment | 991 | 460 | — | — | — |
| Feed | 993 | 459 | 44 | 66 | 48 |
| 2 hr. Steam Treatment | 1085 | 460 | — | — | — |
| Feed | 1085 | 460 | 91 | 60 | 92 |

The data in Table 6 below illustrate: that carbon tetrachloride activations become effective between about 260° and 300° C; conversion is substantially adversely affected at activation temperatures above 400° C; and maximum selectivity increases are observed above activation temperatures of about 360° C.

ation will take place. Successful reactivations have occurred at rates of addition of $2 \times 10^{-4}$ ml $CCl_4$/sec. into the feed passed over about 4 grams of catalyst. Unsuccessful reactivations have occurred on 4 gram catalyst beds at $CCl_4$ additions to the feed passed over the catalyst bed at rates of $2 \times 10^{-8}$ and $2 \times 10^{-5}$ ml

TABLE 6

| Test Description | Reactor Temp., C. | Conversion, Percent | Selectivity, Percent | Weight Yield Percent |
|---|---|---|---|---|
| 260° C Activation | | | | |
| Base | 450 | 99 | 35 | 58 |
| $CCl_4$ Activation | 260 | — | — | — |
| Post Activation | 450 | 99 | 35 | 58 |
| 300° C. Activation | | | | |
| Base | 450 | 98 | 34 | 56 |
| $CCl_4$ Activation | 300 | — | — | — |
| Post Activation | 450 | 97 | 54 | 88 |
| $CCl_4$ Activation | 300 | — | — | — |
| Post Activation | 450 | 96 | 56 | 91 |
| 330° C Activation | | | | |
| Base | 450 | 99 | 32 | 53 |
| $CCl_4$ Activation | 330 | — | — | — |
| Post Activation | 450 | 94 | 52 | 82 |
| Post Activation | 409 | 84 | 64 | 91 |
| $CCl_4$ Activation | 330 | — | — | — |
| Post Activation | 450 | 95 | 56 | 90 |
| $CCl_4$ Activation | 330 | — | — | — |
| Post Activation | 450 | 93 | 59 | 93 |
| 356° C Activation | | | | |
| Base | 450 | 97 | 34 | 56 |
| $CCl_4$ Activation | 356 | — | — | — |
| Post Activation | 450 | 93 | 48 | 75 |
| $CCl_4$ Activation | 356 | — | — | — |
| Post Activation | 450 | 91 | 53 | 82 |
| 400° C. Activation | | | | |
| Base | 450 | 98 | 35 | 58 |
| $CCl_4$ Activation | 400 | — | — | — |
| Post Activation | 450 | 90 | 63 | 97 |
| 450° C. Activation | | | | |
| Base | 450 | 94 | 33 | 59 |
| $CCl_4$ Activation | 450 | — | — | — |
| Post Activation | 450 | 50 | 66 | 56 |

EXAMPLE 8

In this example various catalysts were analyzed for chloride content after certain operations had been performed thereon. All the catalysts used were unsupported phosphorous-vanadium-oxygen complexes containing a zinc metal promoter with an atomic ratio of P:V:Zn of about 1.15/1/0.2.

A spent catalyst which had been on stream for a period of time to deactivate it somewhat was found to contain about 0.02 weight percent Cl. This catalyst was not contacted during its life with reactivating agents. Its only process use was in converting a 1.4 mole percent butane in air feed to a maleic anhydride product.

A second catalyst which had become activated by contact with a butane-air feed mixture was treated with $CCl_4$ in a nitrogen purge by passing about 0.1 grams of $CCl_4$ over a 15 second period resulting in a WHSV of about 1.43 through the catalyst bed at a temperature above 300° C. Three hours after the $CCl_4$ treatment the nitrogen purge was stopped and the catalyst was cooled. The catalyst was found to contain 0.02 weight percent Cl.

A third catalyst deactivated and treated with $CCl_4$ as described above was then treated with steam as described in Example 6 for two hours. Then a three hour nitrogen purge took place. The resulting catalyst was found to contain 0.01 weight percent Cl.

EXAMPLE 9

The rates of addition of $CCl_4$ appear to be relatively important in determining whether a successful regener- $CCl_4$/sec. A most desirable minimum rate of addition for the 4 gram catalyst beds is around $1 \times 10^{-5}$ ml $CCl_4$/sec.

I claim as my invention:

1. In a process for the preparation of maleic anhydride from the oxidation of feed materials selected from the group consisting of alkanes, alkenes, or mixtures thereof or aromatics which comprises contacting said feed material and a gas containing molecular oxygen in the vapor phase with a solid catalyst comprising a phosphorus-vanadium-oxygen complex having from about 0.5 to about 5 atoms of phosphorus for each atom of vanadium, wherein the improvement comprises contacting said catalyst complex at reactivating conditions with an effective amount of a reactivating agent selected from the group consisting of:
   A. Molecular halogens;
   B. Organic halides being in the vapor state above about 250° C. at atmospheric pressure represented by the formula:

$$c(X)n$$

where each X is selected halide and n is an integer from 1 to 4, any remaining radicals being hydrogen;
   C. Organic halides being in the vapor state above about 250° C. at atmospheric pressure represented by the formula:

$$R(X_1)m$$

where R is alkane, alkene or alkyne of straight or branched structure having at least two carbon atoms and $X_1$ is independently a primary, secondary or tertiary halide and m is an integer of from 1 to about 20 consistent with the number of carbon atoms of said structure; and D. Hydrogen halides;

or mixtures thereof to thereby enhance the selectivity of the catalyst for the production of maleic anhydride.

2. The process of claim 1 further characterized in that said catalyst contains a metal promoter selected from the group consisting of zinc, copper, bismuth, lithium or mixtures thereof.

3. The process of claim 2 further characterized in that said catalyst contains from about 1 to about 1.5 atoms of phosphorous for each atom of vanadium.

4. The process of claim 3 further characterized in that the promoter is zinc and is present as from about 0.01 to about 0.3 atoms of zinc for each atom of vanadium.

5. The process of claim 4 further characterized in that said reactivating agent is selected from the group consisting of $CCl_4$, $CHCl_3$, $CH_2Cl_2$, HCl, $Cl_2$, $CH_3Cl$ or mixtures thereof.

6. The process of claim 4 further characterized in that said reactivating agent is $CCl_4$.

7. The process of claim 1 further characterized in that said feed material comprises normal butane, said catalyst contains from about 1 to about 1.5 atoms of phosphorous per atom of vanadium and a zinc metal promoter present as from about 0.01 to about 0.3 atoms of zinc for each atom of vanadium, and said reactivating agent comprises carbon tetrachloride.

8. The process of claim 1 further characterized in that R has less than 4 carbon atoms and is alkane or alkene and m is an integer of from 1 to about 8 consistent with the number of carbon atoms of said structure, and said hydrogen halide is HCl.

9. The process of claim 8 further characterized in that said catalyst contains from about 1 to about 1.5 atoms of phosphorous per atom of vanadium and from about 0.01 to about 0.3 atoms of a zinc metal promoter per atom of vanadium.

10. In a process for the production of maleic anhydride from the oxidation of feed materials selected from the group consisting of alkanes, alkenes or mixtures thereof which comprises contacting said feed materials and a gas containing molecular oxygen in the vapor phase with a solid catalyst comprising a phosphorus -vandadium-oxygen complex, said catalyst complex having from about 0.5 to about 5 atoms of phosphorus for each atom of vanadium, wherein the selectivity of the catalyst for production of maleic anhydride from said feed materials has decreased from a level achieved during earlier catalyst life of said catalyst complex, wherein the improvement comprises contacting said catalyst complex with an effective amount of a reactivating agent selected from the group consisting of:

A. Molecular halogens;
B. Organic halides being in the vapor state above about 250° C. at atmospheric pressure represented by the formula:

wherein each X is a selected halide and n is an integer from 1 to 4 any remaining radicals being hydrogen;

C. Organic halides being in the vapor state above about 250° C. at atmospheric pressure represented by the formula:

where R is alkane, alkene or alkyne of straight or branched structure having at least two carbon atoms, each $X_1$ is independently a primary, secondary or tertiary halide and m is an integer of from 1 to about 20 consistent with the number of carbon atoms of said structure; and D. Hydrogen halides;

or mixtures thereof to thereby enhance the selectivity of the catalyst for the production of maleic anhydride.

11. The process of claim 10 further characterized in that R has less than 4 carbon atoms and is alkane, m is an integer of from 1 to 8 consistent with the number of carbon atoms of said structure and said hydrogen halide is HCl.

12. The process of claim 10 further characterized in that said feed materials comprise normal butane.

13. The process of claim 11 further characterized in that said catalyst contains from about 1 to about 1.5 atoms of phosphorous for each atom of vanadium and from about 0.01 to about 0.3 atoms of a zinc promoter per atom of vanadium.

14. The process of claim 11 further characterized in that said feed materials comprise normal butane, said catalyst contains from about 1 to about 1.5 atoms of phosphorous and from about 0.01 to about 0.3 atoms of a zinc metal promoter for each atom of vanadium.

15. In a process for the preparation of maleic anhydride which comprises contacting a feed material comprising butane and a gas containing molecular oxygen in the vapor phase with a solid catalyst comprising a phosphorus -vanadium-oxygen complex, said catalyst complex having from about 0.5 to about 5 atoms of phosphorus for each atom of vanadium, wherein the improvement comprises contacting said catalyst complex at reactivating conditions with an effective amount of a reactivating agent containing a material selected from the group consisting of:

A. Molecular halogens;
B. Organic halides being in the vapor state above about 250° C. at atmospheric pressure represented by the formula:

where each X is a selected halide and n is an integer from 1 to 4 any remaining radicals being hydrogen;

C. Organic halides represented by the formula:

where R is alkane, alkene or alkyne having from two to three carbon atoms, each $X_1$ is independently a primary, secondary or tertiary halide and m is an integer of from 1 to about 8 consistent with the number of carbon atoms of said structure: and D. Hydrogen halides;

or mixtures thereof to thereby enhance the selectivity of the catalyst for the production of maleic anhydride.

16. The process of claim 15 further characterized in that said catalyst complex contains a metal promoter selected from the group consisting of zinc, copper, bismuth, lithium or mixtures thereof, the atomic ratio of phosphorous to vanadium being from about 1 to about 1.5.

17. The process of claim 16 further characterized in that said metal promoter comprises zinc.

18. The process of claim 16 further characterized in that said reactivating agent comprises carbon tetrachloride.

19. The process of claim 16 further characterized in that said reactivating conditions include addition of reactivating agent to the feed material.

20. The process of claim 16 further characterized in that said reactivating conditions include contacting a gaseous stream containing said reactivating agent in the absence of molecular oxygen with said catalyst complex.

21. The process of claim 16 further characterized in that said reactivating agent is selected from the group consisting of $CCl_4$, $CHCl_3$, $CH_2Cl_2$, $CH_3Cl$, $CF_4$, HCl, $Cl_2$, trichloroacetic acid and mixtures thereof.

22. The process of claim 10 further characterized in that said reactivating agent is $CCl_4$.

23. The process of claim 14 further characterized in that said reactivating agent is $CCl_4$.

24. The process of claim 15 further characterized in that said reactivating agent comprises $CCl_4$.

25. The process of claim 15 further characterized in that said reactivating conditions include contacting a gaseous stream containing said reactivating agent in the absence of butane with said catalyst complex.

26. The process of claim 15 further characterized in that said reactivating conditions include contacting a gaseous stream containing said reactivating agent in the absence of butane and molecular oxygen with said catalyst complex.

27. In a process for the preparation of maleic anhydride which comprises contacting a feed material comprising butane and a gas containing molecular oxygen in the vapor phase with a solid catalyst comprising a phosphorus-vanadium-oxygen complex, said catalyst complex having from about 0.5 to about 5 atoms of phosphorus for each atom of vanadium wherein the improvement comprises contacting said catalyst complex at reactivating conditions including the absence of feed butane with an effective amount of a reactivating agent containing a material selected from the group consisting of:

A. Molecular halogens;
B. Organic halides being in the vapor state above about 250° C. at atmospheric pressure represented by the formula:

$$C(X)_n$$

where each X is a selected halide and $n$ is an integer from 1 to 4 any remaining radicals being hydrogen;

C. Organic halides represented by the formula:

$$R(X_1)_m$$

where R is alkane, alkene or alkyne having from two to three carbon atoms, each $X_1$ is independently a primary, secondary or tertiary halide and m is an integer of from 1 to about 8 consistent with the number of carbon atoms of said structure; and D. Hydrogen halides; or mixtures thereof to thereby enhance the selectivity of the catalyst for the production of maleic anhydride.

28. The process of claim 27 further characterized in that said catalyst complex contains a metal promoter selected from the group consisting of zinc, copper, bismuth, lithium or mixtures thereof, the atomic ratio of phosphorus to vanadium being from about 1 to about 1.5.

29. The process of claim 28 further characterized in that said metal promoter comprises zinc.

30. The process of claim 28 further characterized in that said reactivating agent comprises carbon tetrachloride.

31. The process of claim 27 further characterized in that said reactivating conditions include a temperature of less than about 400° C.

32. The process of claim 27 further characterized in that said reactivating conditions include a temperature in the range of from about 300° to about 500° C.

33. The process of claim 32 further characterized in that said reactivating conditions include a steam treatment following contact of said catalyst with reactivating agent.

34. The process of claim 1 further characterized in that said reactivating conditions include a temperature of less than about 400° C.

35. The process of claim 1 further characterized in that said reactivating conditions include a temperature in the range of from about 300° to about 500° C.

36. The process of claim 35 further characterized in that said reactivating conditions include a steam treatment following contact of said catalyst with reactivating agent.

37. The process of claim 10 further characterized in that said reactivating conditions include a temperature of less than about 400° C.

38. The process of claim 10 further characterized in that said reactivating conditions include temperature in the range of from about 300° to about 500° C.

39. The process of claim 38, further characterized in that said reactivating conditions include a steam treatment following contact of said catalyst with reactivating agent.

40. The process of claim 15 further characterized in that said reactivating conditions include a temperature of less than about 400° C.

41. The process of claim 15 further characterized in that said reactivating conditions include a temperature in the range of from about 300° to about 500° C.

42. The process of claim 41 further characterized in that said reactivating conditions include a steam treatment following contact of said catalyst with reactivating agent.

43. The process of claim 1 further characterized in that said reactivating agent is selected from the group consisting of $CCl_4$, $CHCl_3$, $CH_2Cl_2$, HCl, $Cl_2$, $CH_3Cl$ or mixtures thereof.

44. The process of claim 1 further characterized in that said reactivating agent comprises carbon tetrachloride.

45. The process of claim 12 further characterized in that said reactivating agent is selected from the group consisting of $CCl_4$, $CHCl_3$, $CH_2Cl_2$, HCl, $Cl_2$, $CH_3Cl$ or mixtures thereof.

46. The process of claim 17 further characterized in that said reactivating agent is selected from the group consisting of $CCl_4$, $CHCl_3$, $CH_2Cl_2$, HCl, $Cl_2$, $CH_3Cl$ or mixtures thereof.

47. The process of claim 29 further characterized in that said reactivating agent is selected from the group consisting of $CCl_4$, $CHCl_3$, $CH_2Cl_2$, HCl, $Cl_2$, $CH_3Cl$ or mixtures thereof.

48. The process of claim 29 further characterized in that said reactivating agent comprises carbon tetrachloride.

* * * * *